US010157313B1

United States Patent
Zhang et al.

(10) Patent No.: US 10,157,313 B1
(45) Date of Patent: Dec. 18, 2018

(54) 3D GAZE CONTROL OF ROBOT FOR NAVIGATION AND OBJECT MANIPULATION

(71) Applicant: Colorado School of Mines, Golden, CO (US)

(72) Inventors: Xiaoli Zhang, Arvada, CO (US); Songpo Li, Golden, CO (US)

( * ) Notice: Subject to any disclaimer, the term of this patent is extended or adjusted under 35 U.S.C. 154(b) by 24 days.

(21) Appl. No.: 14/860,664

(22) Filed: Sep. 21, 2015

Related U.S. Application Data

(60) Provisional application No. 62/052,900, filed on Sep. 19, 2014, provisional application No. 62/052,931, filed on Sep. 19, 2014.

(51) Int. Cl.
    *G06K 9/00*     (2006.01)
    *G06T 7/40*     (2017.01)

(52) U.S. Cl.
    CPC ....... *G06K 9/00617* (2013.01); *G06K 9/0061* (2013.01); *G06K 9/00604* (2013.01); *G06T 7/408* (2013.01)

(58) Field of Classification Search
    CPC ........... G06K 9/00617; G06K 9/00604; G06K 9/0061; G06T 7/408
    See application file for complete search history.

(56) References Cited

U.S. PATENT DOCUMENTS

| | | | | |
|---|---|---|---|---|
| 5,689,619 A | * | 11/1997 | Smyth | G02B 27/0093 345/156 |
| 8,885,882 B1 | | 11/2014 | Reale et al. | |
| 2010/0321482 A1 | * | 12/2010 | Cleveland | G06F 3/012 348/78 |
| 2014/0300538 A1 | * | 10/2014 | Rijnders | G06F 3/013 345/156 |
| 2016/0018639 A1 | * | 1/2016 | Spitzer | G02B 5/30 345/156 |

OTHER PUBLICATIONS

Abbott et al., "Ultra-low-cost 3D gaze estimation: an intuitive high information throughput compliment to direct brain-machine interfaces," Journal of Neural Engineering, 2012, pp. 1-11, vol. 9.
Hennessey et al., "Noncontact Binocular Eye-Gaze Tracking for Point-of-Gaze Estimation in Three Dimensions," IEEE Transactions on Biomedical Engineering, Mar. 2009, pp. 790-799, vol. 56, No. 3.
Lee, et al., "3D gaze tracking method using Purkinje images on eye optical model and pupil," Optics and Lasers in Engineering, 2012, pp. 736-751, vol. 50.

* cited by examiner

*Primary Examiner* — David F Dunphy
(74) *Attorney, Agent, or Firm* — Dorsey & Whitney LLP

(57) ABSTRACT

Disclosed herein are devices, methods, and systems for controlling a robot or assistive device that allows the robot or device to find and manipulate objects in a real world environment. The disclosed devices, methods, and systems may, in many cases, receive control input through monitoring, tracking, and analyzing the 3D gaze of a user/controller. Using the described 3D eye tracking, a user can directly and naturally look at an object of interest in the real world, while the system monitors, tracks, and records the user's 3D gaze position. This information, in many cases, is then translated into input commands for the robot or assistive.

12 Claims, 10 Drawing Sheets

(5 of 10 Drawing Sheet(s) Filed in Color)

From pupil ROI

From entire image

Glint identification

3D GAZE CONTROL OF ROBOT FOR NAVIGATION AND OBJECT MANIPULATION

CROSS REFERENCE TO RELATED APPLICATIONS

This application claims benefit of priority pursuant to 35 U.S.C. § 119(e) of U.S. provisional patent application Nos. 62/052,900 and 62/052,931 filed Sep. 19, 2014 both of which are hereby incorporated by reference in their entirety.

STATEMENT REGARDING RESEARCH & DEVELOPMENT

This invention was made with Government support under award number: CBET-1414299 awarded by the National Science Foundation. The Government has certain rights in the invention.

FIELD

The disclosed processes, methods, and systems are directed to detecting and tracking a gaze point of a user in three-dimensional space as well as generating control signal for a robotic device based on the gaze point.

BACKGROUND

Existing control systems using gaze-monitoring as an input are very limited. Gaze recognition has been limited to relatively simple commands, such as button trigger and keyboard typing. One barrier of gaze-controlled robot manipulation is the lack of volumetric or three-dimensional information and/or depth of field information. Current gaze tracking technologies rely on 2D gaze-tracking on a computer display. This limits the number and type of commands that can be given.

Fundamentally, the eye is a perceptual organ that is not typically for an input into robotic or other control systems. Therefore, using solely gaze as a control input signal requires a system that can differentiate between normal behavioral eye movements and intentional eye "commands." This issue of differentiation is known as the Midas touch problem. The "Midas touch problem" is that the eyes cannot be used directly as controllers (such as a mouse), because the eyes are rarely "off." Thus, a "select" or "click" command is usually derived from tedious eye gestures (such as excessive blinks, deliberate dwell time, other controlled eye movements) as a confirmation to a specific command from the eye.

The emergence of assistive robotic techniques holds the hope to restore vital degrees of independence to the elderly and disabled in activities of daily living (ADL), improving their quality of life. However, conventional control of assistive robotic devices, such as wheelchairs or robotic prosthetics, relies on the user's physical motion/gesture through a device such as joystick, button, infrared laser or verbal communication. These input methods may bring physical and mental burdens on the user, especially for those with mobility disability or verbal impairment.

Existing gaze tracking robotic device control systems are generally cumbersome to the user by requiring incremental control of the robotic device. Accordingly, there is a need for a gaze tracking method and system wherein the robot control system and method does not require tedious eye gestures. Furthermore, there is a need for such as system which allows for a user to control the robotic device, such as a robotic assistive device, in a smooth and continuous manner and at different speeds based solely on the gaze position of their eyes.

SUMMARY

Disclosed herein are devices, methods, and systems for tracking a user's gaze point in three dimensions as well as using said gaze point to control a robotic device or robotic assistive device, thus allowing the robotic device to navigate in 3D space, or find and manipulate objects in a real world environment. The disclosed devices, methods, and systems may, in many cases, receive control input through monitoring, tracking, and analyzing the 3D gaze of a user/controller. Using the described 3D eye tracking, a user can directly and naturally look at an object of visual interest in the real world, while the system monitors, tracks, and records the user's 3D gaze position. This information, in many cases, is then translated into input commands for the robotic device or robotic assistive device.

Disclosed herein are methods, devices, and systems for extracting eye features through the monitoring and analysis of pupillary responses and eye movement patterns. In many embodiments, these responses and patterns represent intentional manipulatory gaze "commands," which are distinguished from scanning eye movements. The systems and devices described herein may use intelligent fuzzy algorithms or neural networks to utilize the detected eye features and patterns to form an automatic visual intention differentiation and visual and/or cognitive interest recognition methods.

In many embodiments, a user's manipulatory intention may be recognized, monitored and analyzed using an intelligent fuzzy logic method. Use of a fuzzy logic method may result in enhancing correlation of gaze features, and increasing the effective fusion of correlated gaze features for automated recognition. Additionally, use of fuzzy logic may increase the accuracy and responsiveness of the disclosed systems and devices.

In many embodiments, eyes are monitored by a binocular head-mounted tracking system coupled to 3D gaze estimating computer modules. The head-mounted tracking system gathers input from the movements of the eyes and pupils, and analyzes the information in order to produce an output that may then be used to aid in manipulating/controlling a robot that may then interact with its surroundings/environment. In many cases, eye and pupillary movements may be correlated with motor intentions and cognition interests. As discussed above, the tracking of eye and pupil movement may provide an intuitive, effortless, and effective method to communicate signals from a person with motor impairment to a robotic or assistive device.

Disclosed herein are devices, methods, and systems for controlling a robot or assistive device through monitoring, recognition, and analysis of eye and pupil movement to allow control of a robotic device in three dimensions based on tracking a user's gaze in three dimensions. In many embodiments, a rule-based gaze control system, device, or method may aid in robot navigation and object manipulation. The disclosed systems, methods, and devices may aid in keeping control procedures simple and may aid in reducing the control complexity for human beings.

While multiple embodiments are disclosed, still other embodiments of the present invention will become apparent to those skilled in the art from the following detailed description. For example, 3D gaze tracking may be used to control and interact with electronic, non-robotic devices such as computers, virtual reality environments, and the like. As will be apparent, the invention is capable of modifications in various obvious aspects, all without departing from the spirit and scope of the present invention. Accordingly, the detailed description is to be regarded as illustrative in nature and not restrictive.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
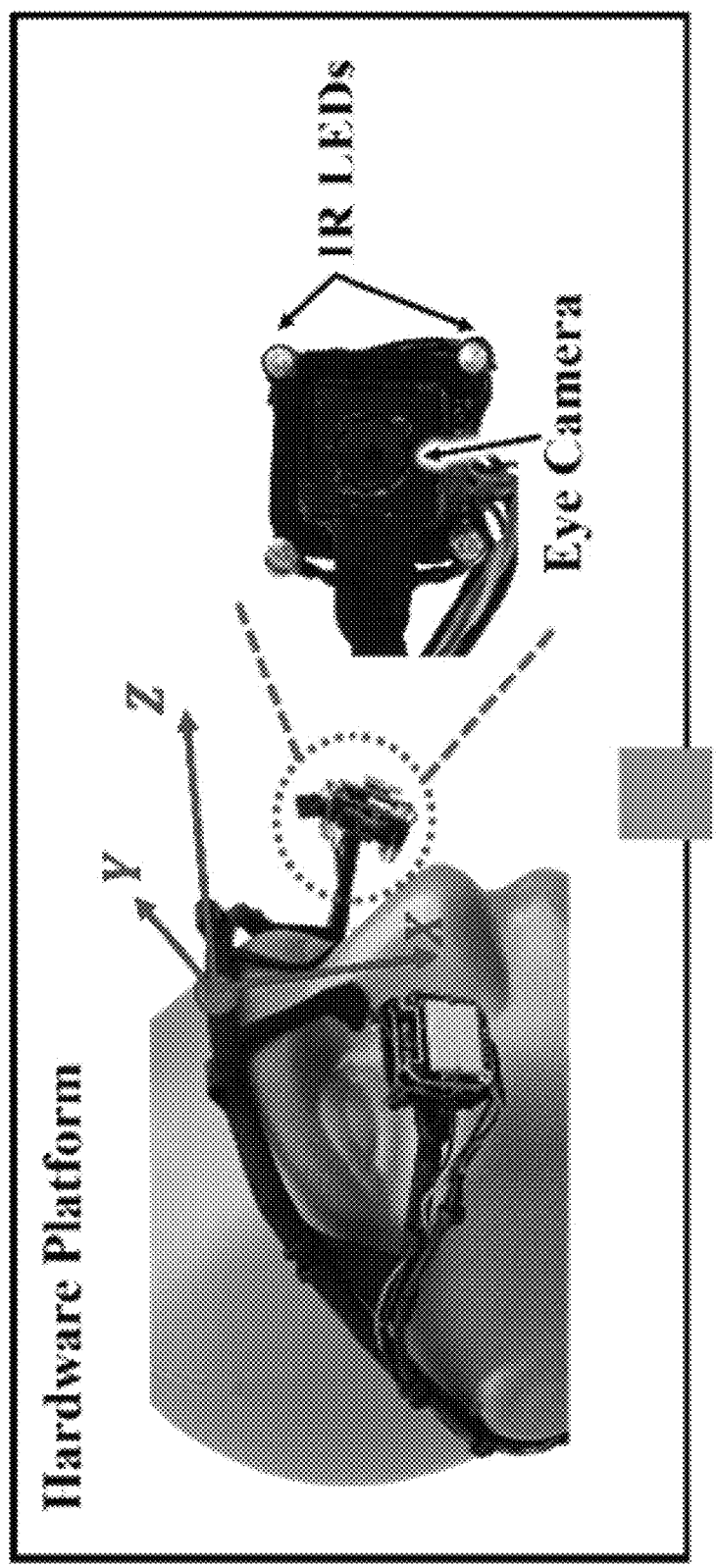
FIG. 1 is an overview of one embodiment of a hardware platform in a 3D gaze tracking system.

The emergence of assistive robotic techniques holds the hope to restore vital degrees of independence to the elderly and disabled in activities of daily living (ADL), improving their quality of life. However, current control of assistive robots relies on the user's physical motion/gesture through a device such as joystick, button, infrared laser or verbal communication, which may bring physical and mental burdens on the user, especially for those with mobility disability or verbal impairment. A natural interaction interface between human and robot system is missing. Ideal human-robot interfaces (HRIs) place few cognitive burdens on users, and user inputs are generally intuitive and responsive.

The disclosed systems and methods Lack of 3D eye tracking to provide volumetric information for robot control in the real world. A main barrier of gaze-controlled robot manipulation is the lack of volumetric information. Current gaze tracking technologies are mainly 2D tracking on a computer display. However, for robot to find and manipulate an object in real world, the 3D gaze tracking is needed. With the 3D eye tracking, the user can directly and naturally looking at the object of interest in the real world and the user's 3D gaze position can be tracked and used as the input command for robot to approach.

The present systems and methods help to provide for a natural and implicit way for command confirmation using eye gaze. Fundamentally, the eye is a perceptual organ not meant for an output communication channel. Therefore, using solely gaze as control input signals requires the differentiation of normal behavioral eye movements and intentional eye "commands," which is known as the Midas touch problem (the eyes cannot be used directly as a mouse, because the eyes are never "off." The "select" or "click" command is usually derived from tedious eye gestures (such as excessive blinks, over-long dwell time, other controlled eye movements) as a confirmation to a specific command from the eye). Ideally, gaze-based robot control should be conducted implicitly without tedious eye gestures. In this invention, eye features will be extracted by analyzing pupillary responses and eye movement patterns to represent the intentional manipulatory gaze "commands", and an intelligent fuzzy algorithm is adopted to fuse these eye features for automated and implicit intention recognition. The analysis of pupillary response and gaze movements on the pattern level has three values: a complete understanding of intention manipulatory gazes, increased accuracy and reliability of the intent recognition, and improved interaction speed. The recognition of the user's manipulatory intention using an intelligent fuzzy approach has two benefits: effectively fusion of all the correlated gaze features for automated recognition and increased the accuracy and responsiveness of the system.

The present systems and methods provide for effective and natural robot control strategies using eye gaze. Effective control using gaze is very limited. Gaze has been limited to relative simple commands, such as button trigger and keyboard typing. Using gaze for relative complex robot control, to the inventor's knowledge, does not exist. In this invention, a rule-based gaze control for robot navigation and object manipulation is developed. These rules for object fetching and object transferring are designed with the consideration of several factors: 1. The status of the robot's hands; 2. The relation between two successive tasks; 3. The relation between the robot's current position and the target position; and 4. Emergence and administration features for safety consideration. The aim is to keep the control procedure simple and reduce the control complexity for human beings.

In this disclosure, the eyes are used not only for gathering input from surroundings, but also for producing output to the surroundings. Eye movements are highly correlated with motor intentions and cognition interests and are often retained by motor impaired people including those suffering from muscular dystrophy and motor neuron disease; spinal traumas; paralysis and stroke; amputation; multiple sclerosis and Parkinson's; as well as the rapidly aging population. Therefore, eye tracking provides an intuitive, effortless, and effective communication signal directly relevant for robots. The observer then becomes more than an "active" observer. The inventor develops a 3D gaze-based robot control system to use 3D gaze to guide robots for navigation and object manipulation, where individuals with restricted mobility could use their eyes to operate assistive robots for identifying, approaching, and manipulating target objects. The eyes' advantages of natural sensory nature, cognition-relevance, and volumetric information makes it promising in assistive robotics field. The rationale for these systems and methods is "what you look at is what you get." The present system will: 1) provide a new strategy to determine the position of the target object by monitoring 3D gaze; 2) provide a novel approach to differentiate normal behavioral eye movements from intentional eye "commands"; and 3) provide a natural and effective strategy to use eye gaze data to create robot operation commands.

Existing robot navigation and manipulation using eye gaze inputs are scarce and gaze-based robot control is still in its infancy. Related works about gaze-based robot control include: 1. In case virtual buttons on a display are connected to joint rotation commands of an articulated robot arm such that the subject can steer the arm by 2D gaze on the buttons. 2. In work, a monocular eye tracking system was used to track the gaze vector, which serves as the pointing line along which the robot can search and retrieve the target object. However, a pointing line may have intersections with more than one object; therefore the robot has limitations in a cluttered environment. 3. Gaze movement was also used for wheelchair direction control. Discretization of gaze orientations into up, down, left, and right categories allows mapping to the forward, back, left and right motion of wheelchairs.

Examples

The present disclosure will now be discussed with reference to the included drawings, and particular examples. However, as discussed above still other embodiments of the present invention will become apparent to those skilled in the art without departing from the scope of the detailed description.

With reference to FIG. 1, one embodiment of the disclosed 3D gaze tracking and control system is shown. In this embodiment, a headset is mounted on a user's head. The headset has a pair of protruding arms extending generally downward and forward of the user's eyes. At a terminal end of the protruding arms of the headset an eye-monitoring module is provided. Each eye monitoring module may have at least one camera and a plurality of illumination sources. In some examples, the camera of each eye monitoring module may be sensitive to infrared (IR) light, and the illumination sources may be IR illumination sources. Each eye monitoring module has within its field of view each of a user's eyes, respectively. The camera and illumination sources may be electrically connected to a power source and a controller via power and communication lines. A coordinate system may be established at a center point of the user's eyes. However, other coordinate system origin locations may be used.

Figure 2:
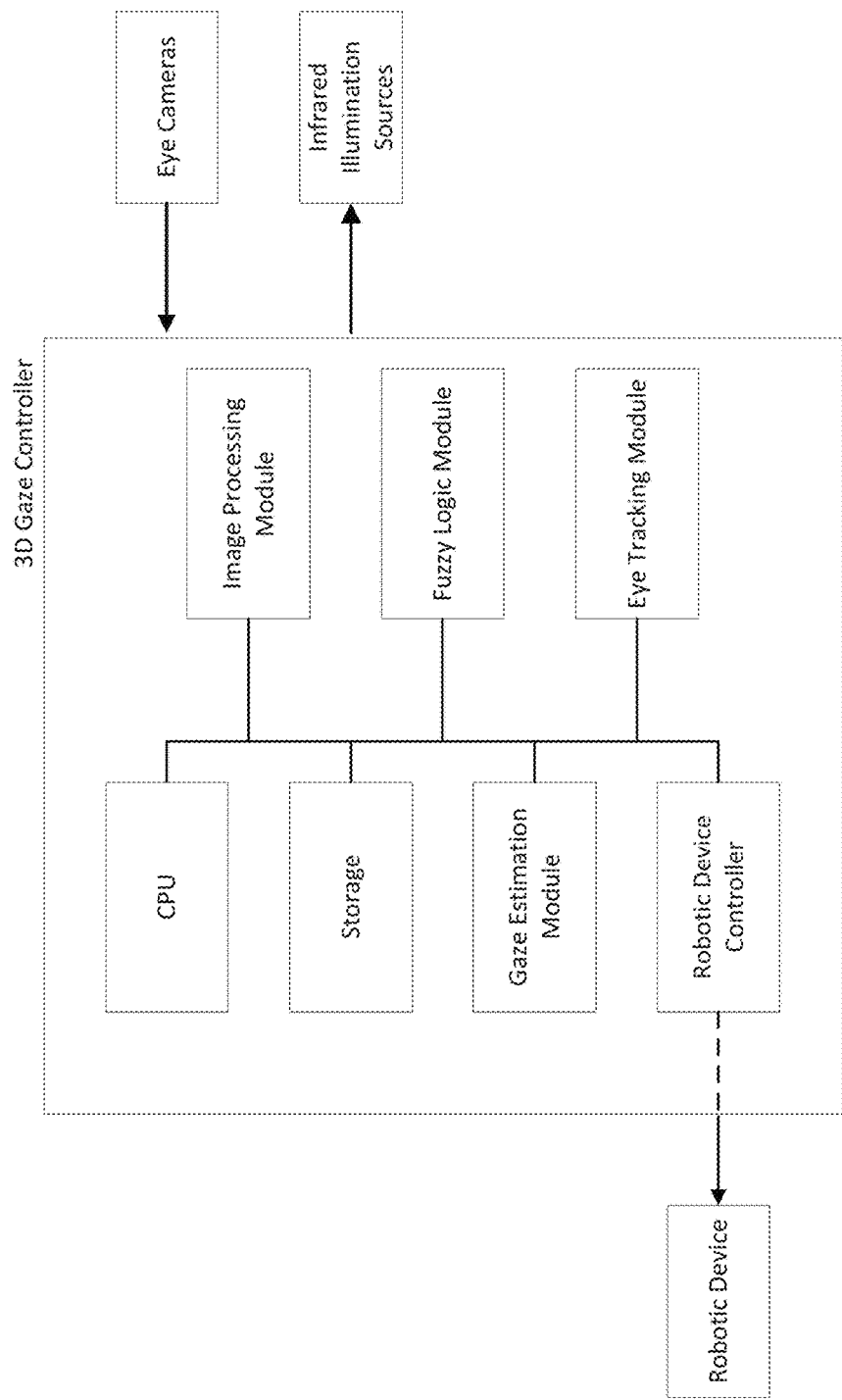
FIG. 2 depicts a circuit diagram for the 3D gaze tracking system

FIG. 2 depicts a circuit diagram for the 3D gaze tracking system. The 3D gaze tracking controller may be provided with a processing element for controlling operations of the 3D gaze tracking system including operation of a robotic device. The 3D gaze tracking controller is further provided with a storage device which may have operation instructions, calibration data, applications for controlling various modules, and the like. An image processing module may input image information from the plural eye cameras, which can process images to extract features of the image used to determine the visual axis of a user's eye for use with the eye tracking module. The 3D gaze controller further controls infrared illumination sources to shine IR light onto each of the user's eyes, respectively. In some examples, more than one IR source is provided, thus projecting a predetermined pattern of reflections or "glints" on the eye.

The eye tracking module may calculate the visual axis vector of each respective eye based on the image data from the eye cameras. A gaze estimation module, in communication with the eye tracking module, may be provided to estimate the gaze direction or gaze vector of a user. In some examples, the gaze vector may have a vector origin at the center point of the user's eyes and a vector head proximal to an intersection point of the visual axis vectors, as discussed in more detail below. In some examples, the gaze estimation module and eye tracking module may utilize or communicate with the fuzzy logic module, which may also be a neural network module, to determine and monitor a visual axis vector for each eye and gaze vector properties for the user.

A robotic device controller may be provided with the 3D gaze controller and be in communication with at least the processing element and gaze estimation module. In some examples, the robotic device controller may be in direct or indirect communication with a robotic device, such as a robotic assistive device. The robotic device controller may be in wired or wireless communication with the robotic device in order to provide control instructions to the robotic device.

Figure 3A:
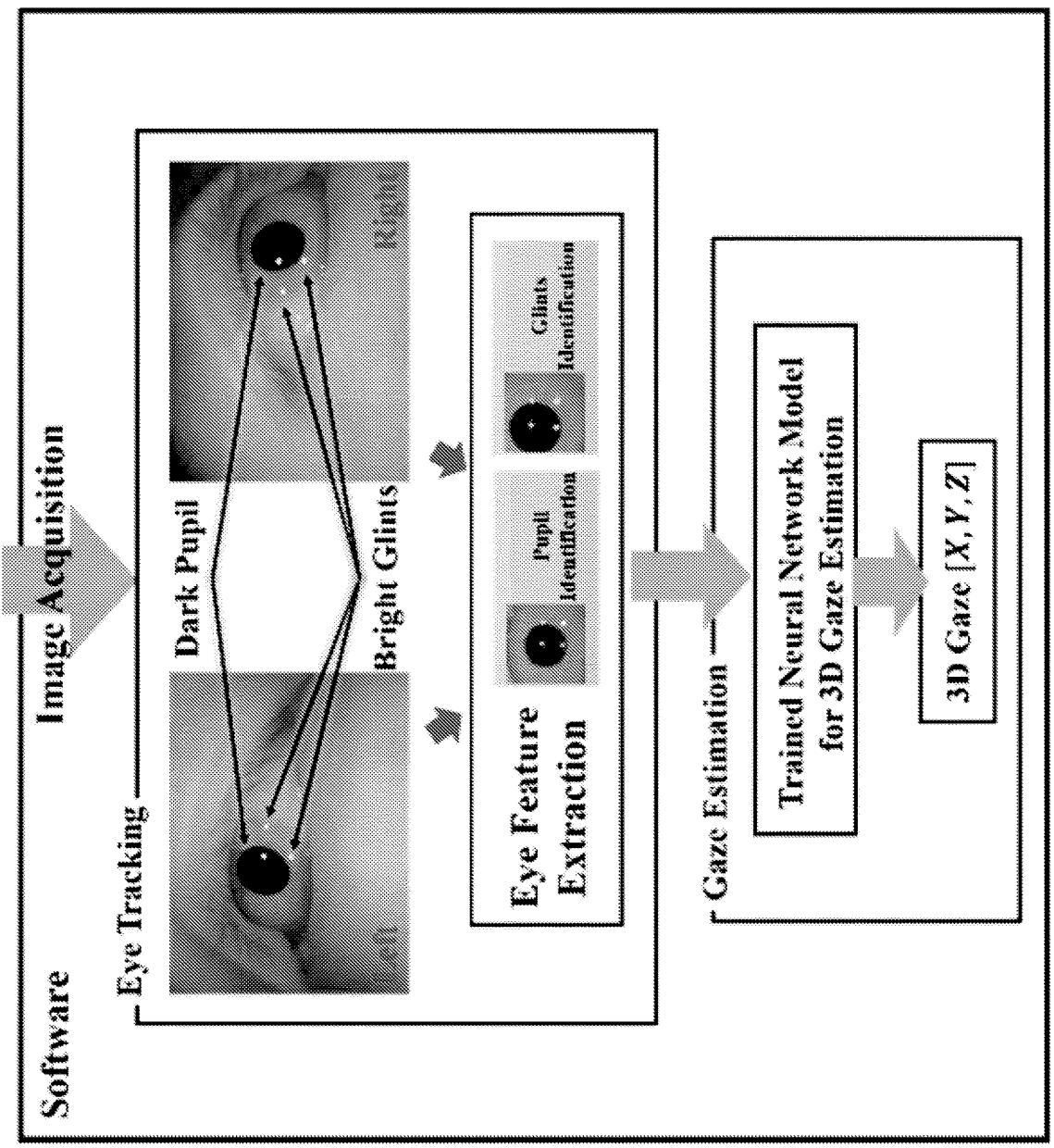
FIG. 3A is an overview of one embodiment of a software platform in a 3D gaze tracking system.
Figure 3B:
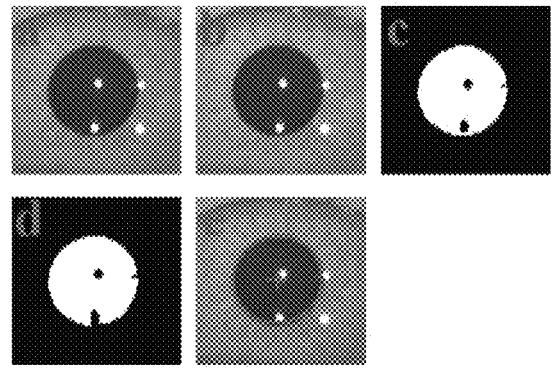
FIG. 3B shows steps of identification of pupil, eye, and glints.
Figure 3B:
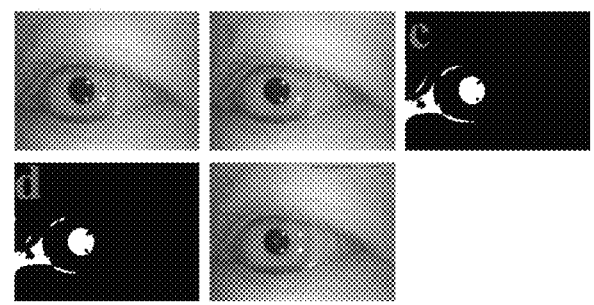
Figure 3B:
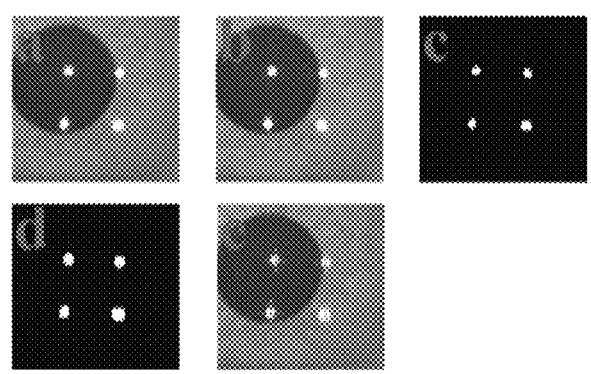
Figure 4:
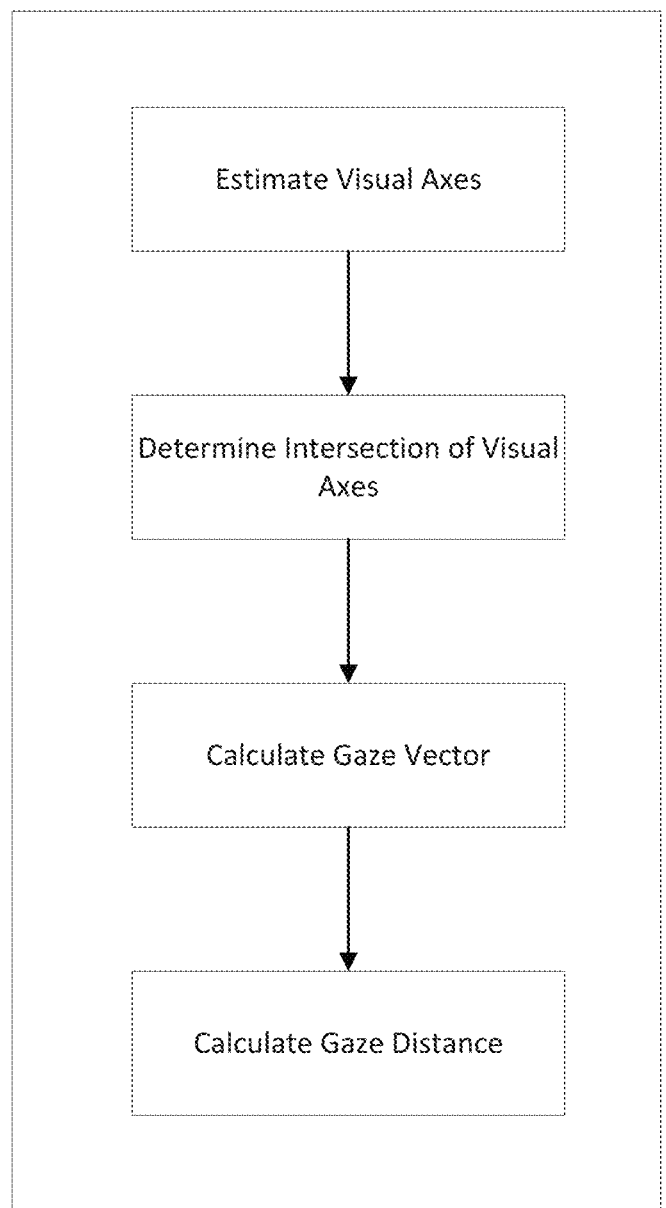
FIG. 4 one embodiment of a process for 3D gaze tracking is described.

Turning now to FIGS. 3 and 4, an overview of the process for detecting and tracking a user's gaze position in 3D space is provided. In FIG. 3A, after image acquisition from the eye cameras, the image processing module determines a pupil location and characteristic, such as dilation or contraction amount. The image processing module may further determine the location of reflected infrared (IR) light beams, which may herein be referred to as "glints." The glints may provide a calibrated or predetermined coordinate system for determining orientation of the eye, pupil, and other characteristics. When eye features have been extracted, the gaze estimation module may determine the location of the user's gaze point in 3D space. That is, the gaze estimation module may determine the position of a point of cognitive or visual interest of the user within a real-world environment in three dimensions.

FIG. 3B shows steps involved in eye, pupil, and glint recognition. The top of FIG. 3B depicts an example of steps of pupil identification from the pupil ROI: (a) raw color image, (b) grayscale image, (c) binary image, (d) binary image after noise elimination, (e) original image with the identified pupil region. The middle of FIG. 3B depicts steps of pupil identification from the entire image: (a) raw color image, (b) grayscale image, (c) binary image, (d) binary image after noise elimination, (e) original image with the identified pupil region. The bottom of FIG. 3B shows steps for glint identification: (a) raw color image, (b) grayscale image, (c) binary image after pixel inversion operation, (d) binary image after noise elimination, (e) original image with identified glint centers.

Figure 5:
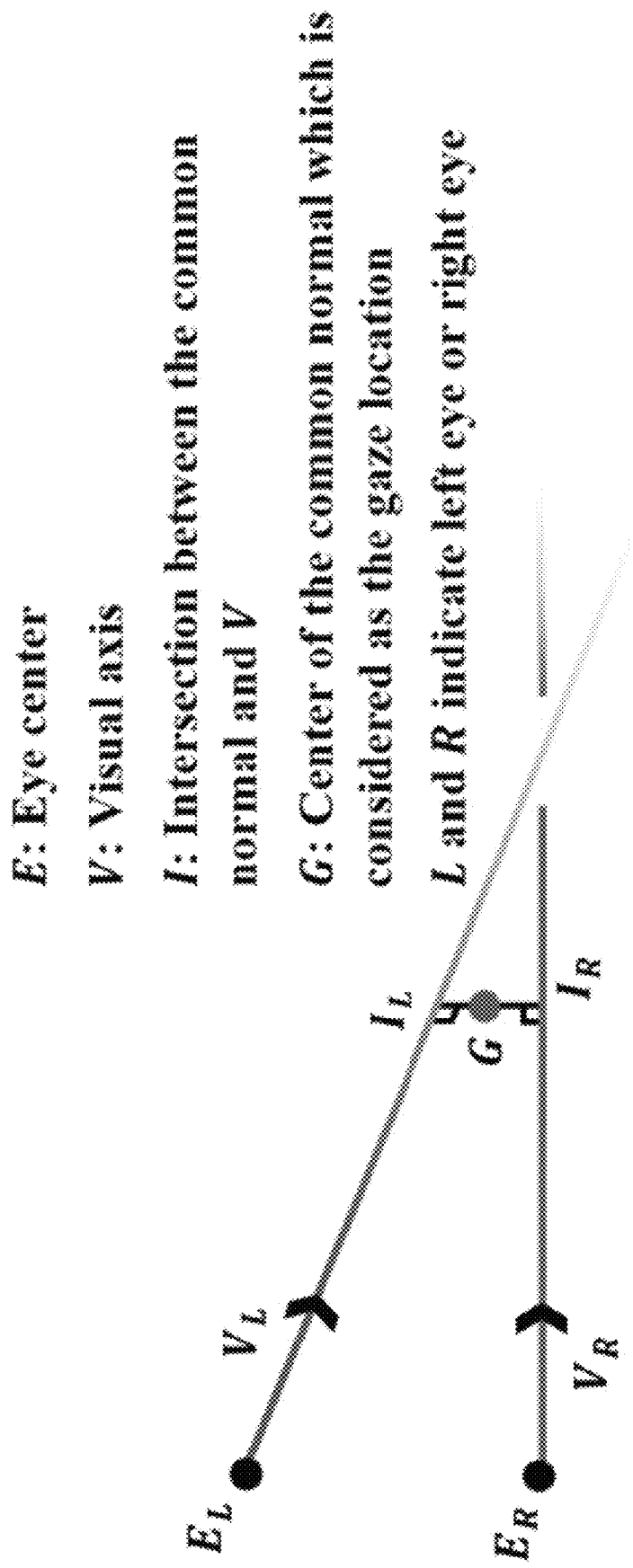
FIG. 5 is an illustration of a visual axes intersection for 3D gaze in one embodiment of use.

With reference to FIG. 4, an example of the 3D gaze tracking process is shown. In step S1, the 3D gaze controller may estimate the visual axes of each of a user's eyes. As shown in FIG. 5, the visual axis $V_L$ of the left eye and the visual axis of the right eye $V_R$ are estimated based on the images detected by the left and right eye cameras, respectively. Each eye's visual axis is estimated using the fuzz logic module or a neural network method, and eye features such as the center of the pupil, pupil shape, and orientation of the pupil are determined. While fuzzy logic modules or neural networks are discussed, regression methods may also be used for the determination of $V_L$ and $V_R$.

Figure 6:
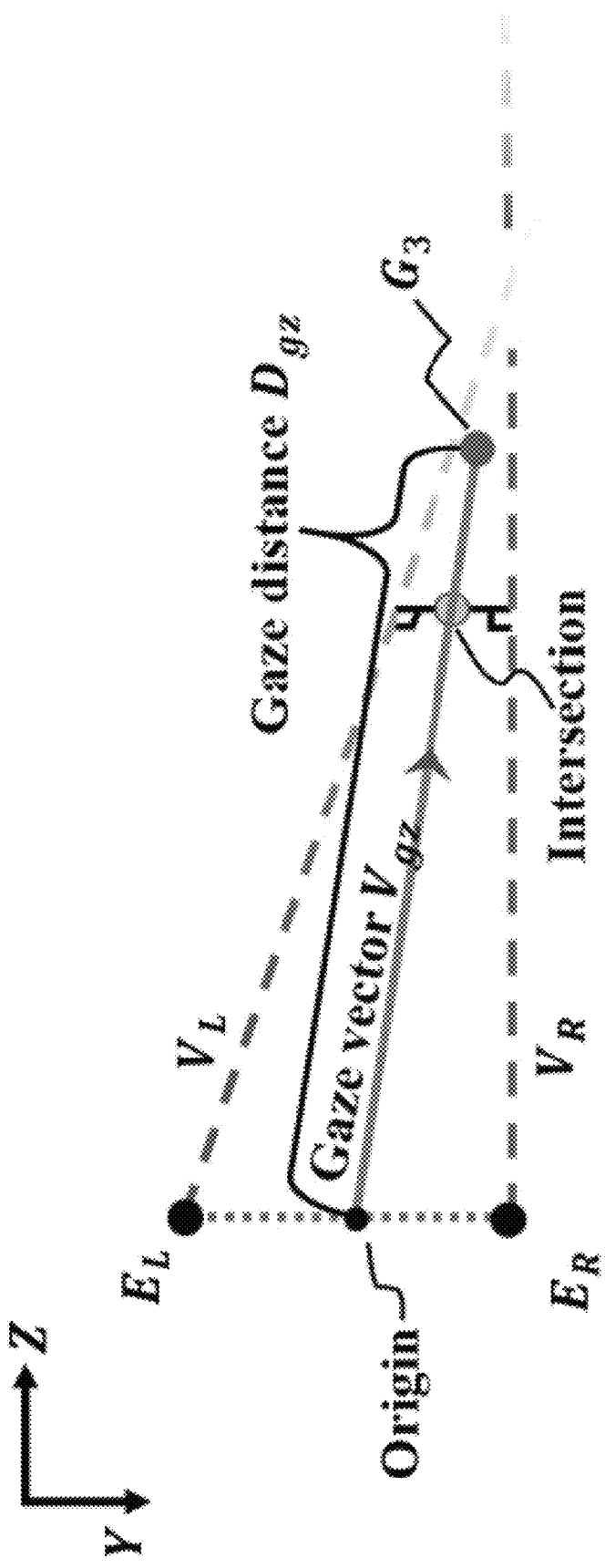
FIG. 6 is a step illustration of a novel 3D gaze in for one embodiment of the disclosed method using the estimation method. This embodiment decouples the estimation of 3D gaze into gaze vector and gaze distance estimations.

At step S2 of FIG. 4, the intersection of the two visual axes is determined as shown in the FIG. 5. Generally, when a user visually concentrates on a location, the visual axes from both eyes intersect at a location in space. However, due to the error associated with determining the estimated visual axes, the two visual axes may not intersect. Thus, in such a case, the 3D gaze controller may determine the point that has shortest distance to both visual axes. This point is considered as the gaze point, which is also the center of the common normal to both visual axes, as shown in FIGS. 5-6.

Once the gaze point has been determined, the operation proceeds to step S3 to calculate the gaze vector. The gaze vector is the connection between the center of the common normal, as discussed above, and the center of the line that connects two eyes, as shown in FIG. 6. When the gaze vector has been calculated, the operation proceeds to step S4 to calculate a gaze distance to a gaze point $G_3$. The gaze distance along the gaze vector direction is estimated using a fuzzy logic or neural network algorithm. Based on the gaze vector and eye features, such as pupil center position, pupil shape, and orientation of the pupil, the gaze distance can be determined as shown in FIG. 6. Thus, the estimation of gaze vector and gaze distance are not decoupled and have been demonstrated to effectively improve the 3D gaze tracking accuracy and increase the size of a tracking workspace.

Figure 7:
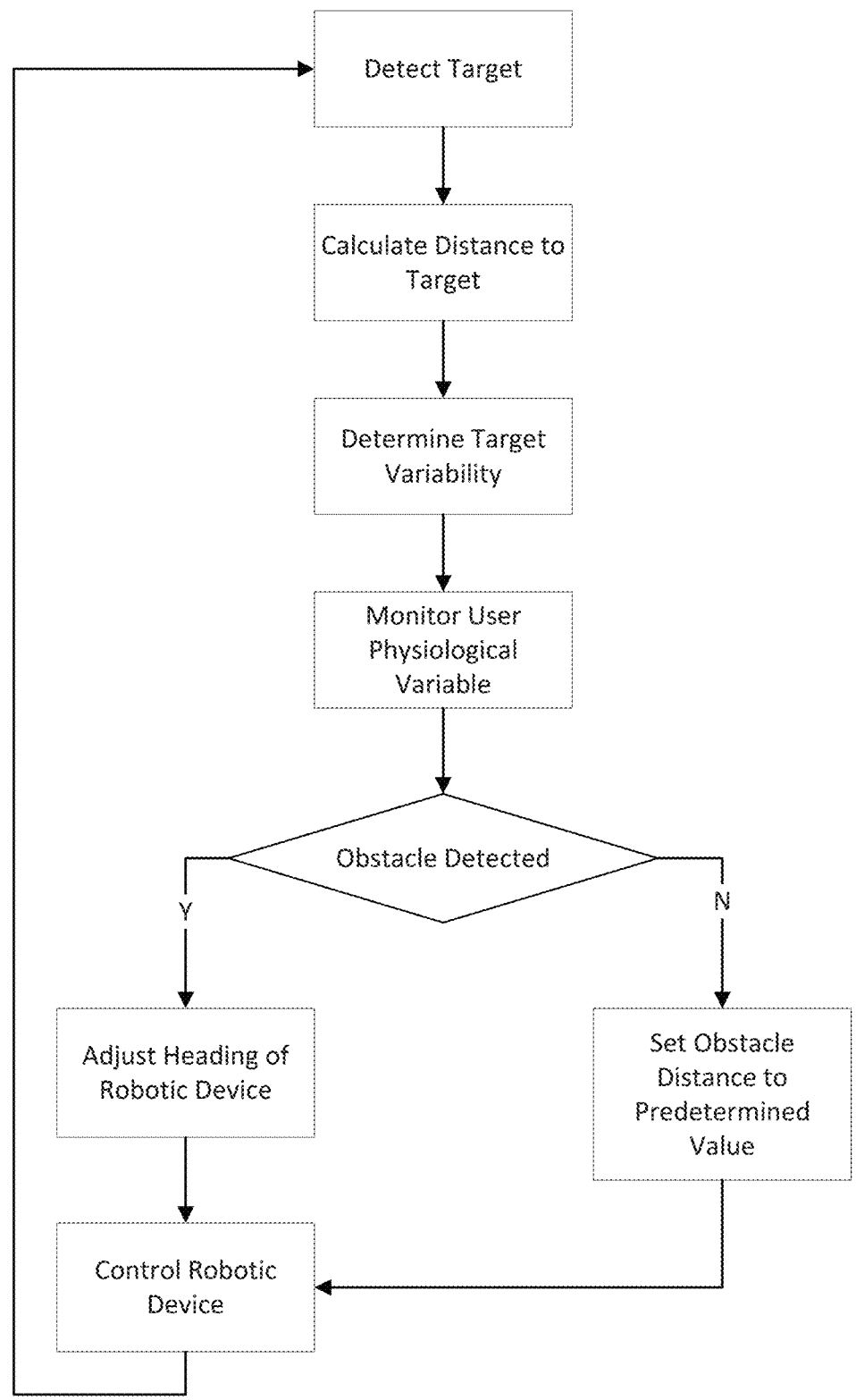
FIG. 7 depicts one embodiment of a process for controlling a robotic device using the robotic device controller in flowchart form is depicted

Referring to FIG. 7, an exemplary process flowchart for controlling a robotic device using the robotic device controller is depicted. In step S1, a target is detected. The target may be the visual or cognitive interest of the user, as determined by the 3D gaze controller. That is, in many examples the target is the gaze point $G_3$ shown in FIG. 6. The target may be determined using a weighted average of the gaze data. In step S2, the target and obstacle distance variables may be calculated using the Pythagorean theorem with Δx and Δy as inputs (see Table 1 below).

At step S3, the process proceeds to determine target variability. Target variability may be represented by the standard deviation of the gaze input data over an averaging window (e.g., a predetermined sampling time). Since target variability is likely to be the input parameter most sensitive to individual characteristics, it may need to be tuned for each individual's "gaze signature." In step S4, the process continues to monitor user physiological variables to determine changes in intended target. During step S5, the process determines if obstacles are detected. If an obstacle is detected, process proceeds to step S6 to adjust the heading of the robotic device in order to avoid the obstacle at step S7. At step S5, if no obstacles were detected in the direct path between the robot and target, the process proceeds to step S8 and the obstacle distance was set to its maximum value of 1 and the process proceeds to control the robotic device in step S7.

Figure 8:
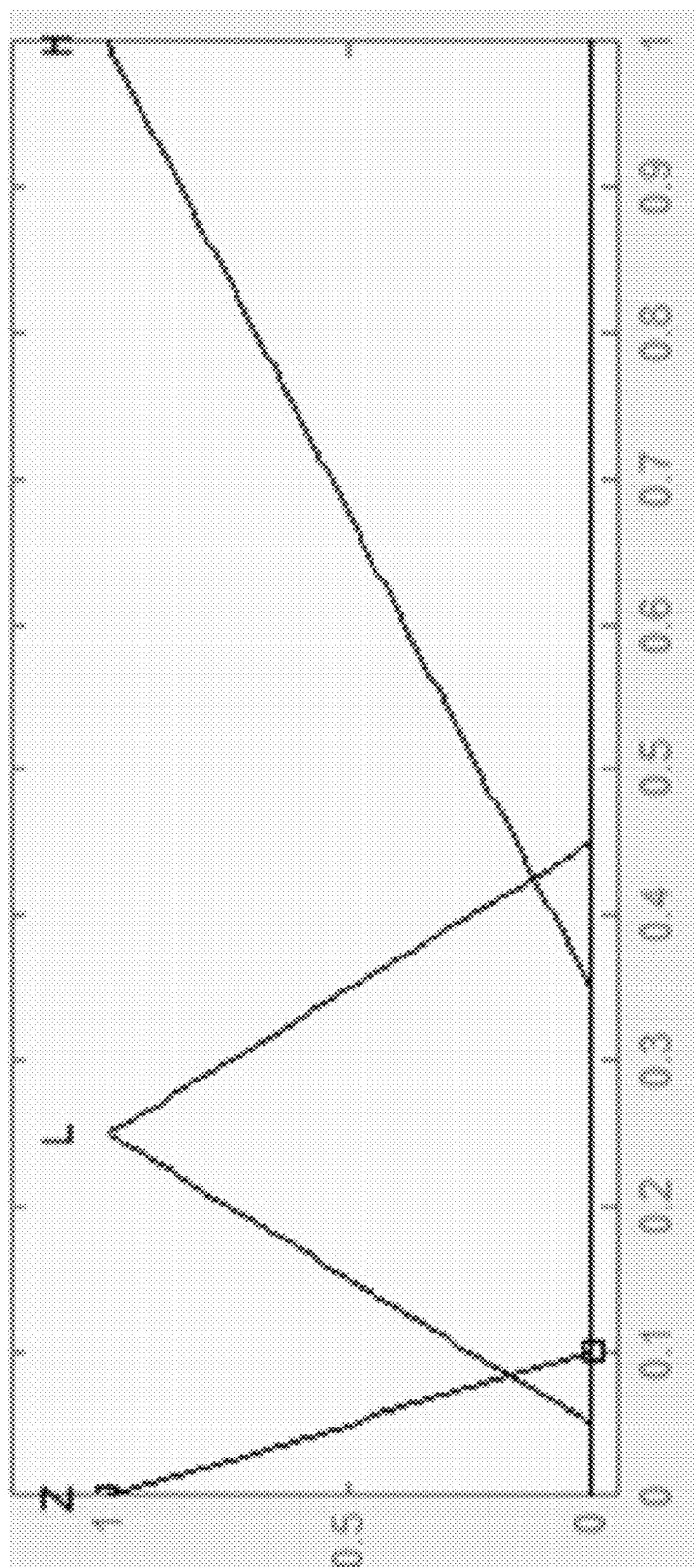
FIG. 8 is a membership function for target variability (Z, zero, L, low, and H, high).

In one particular example, a Mamdani-type fuzzy logic controller with five inputs and three outputs may be created using the Fuzzy Logic Toolbox in MATLAB for use as the fuzzy logic module. The inputs, shown in Table I below, are selected to take into account the control objectives: to track a target at an appropriate speed based on uncertain data while avoiding obstacles. Distance to the target is captured by target Δx and target Δy, the degree of uncertainty of the target's position is expressed by the target variability, and the presence of obstacles in the path from the robot's position to the target is quantified by the obstacle distance. The blink frequency is used to capture operator intent and desired speed. The outputs, also shown in Table I, were used to control the speed and heading of the robot, including steering adjustments for obstacle avoidance. All of the membership functions were triangular, as shown in FIG. 8.

TABLE I

| Input/Output | Variables | | |
|---|---|---|---|
| | Name | Units | Membership Functions |
| I | Target Δx | distance | negative [−1, −0.5, 0]<br>zero [−0.1, 0, 0.1]<br>positive [0, 0.5, 1] |
| I | Target Δy | distance | negative [−1, −0.5, 0]<br>zero [−0.1, 0, 0.1]<br>positive [0, 0.5, 1] |
| I | Target variability | distance | zero [−0.1, 0, 0.1]<br>low [0.05, 0.25, 0.45]<br>high [0.35, 1, 1.4] |
| I | Blink frequency (normalized) | — | zero [−0.4, 0, 0.4]<br>low [0.1, 0.5, 0.9]<br>high [0.6, 1, 1.4] |
| I | Obstacle distance | distance | zero [−0.2, 0, 0.2]<br>low [0, 0.3, 0.6]<br>high [0.35, 1, 1.4] |
| O | Speed | distance/time | zero [−0.4, 0, 0.4]<br>low [0.1, 0.5, 0.9]<br>high [0.6, 1, 1.4] |
| O | Heading | rad | up [0.125, 0.25, 0.375]<br>up/right [0, 0.125, 0.25]<br>right [−0.125, 0, 0.125]<br>down/right [0.75, 0.875, 1]<br>down [0.625, 0.75, 0.875]<br>down/left [0.5, 0.625, 0.75]<br>left [0.375, 0.5, 0.625]<br>up/left [0.25, 0.375, 0.5] |
| O | Heading adjustment | rad | zero [−0.4, 0, 0.4]<br>low [0.1, 0.5, 0.9]<br>high [0.6, 1, 1.4] |

In many embodiments, a target is determined using a weighted average of the gaze data as described previously, the target and obstacle distance variables are then calculated using the Pythagorean theorem, and target variability was represented by the standard deviation of the gaze input data over an averaging window. (In many cases, target variability is likely to be the input parameter most sensitive to individual characteristics, and therefore may need to be adjusted for each individual's gaze "signature." In the present embodiment, target variability was tuned to accommodate the characteristics of the dataset described in above.). Blink frequency is generally normalized to an interval (here [0 1]) by assuming that four blink events within the 20-sample averaging window was high (achieving a value of 1), and lower blinking rates in the same or similar windows of time may receive a proportionally smaller membership value. If no obstacles were detected in the direct path between the robot and target, the obstacle distance may be set to its maximum value of 1. In most embodiments, other distance-based variables do not need to be explicitly normalized since the workspace is generally set up as a unit square. It should also be noted (referring to Table I) that in certain cases (e.g., the "zero" membership functions for target variability, obstacle distance, and blink frequency), negative values (which do not have physical meaning) were used in order to create membership functions for which the lower bound is also the mode, without causing errors in the software.

In the example, the output variables and the maximum speed were constrained to a value of 0.25 (covering one-fourth the workspace in one second at maximum speed), and the maximum heading adjustment for obstacle avoidance was set at ±100°. The heading variable was scaled to allow the robot to steer within the full 360° range.

Fifteen rules were defined to characterize the influence of the five input variables on the three outputs. In particular, four rules capture the influence of the inputs on the output variable speed, eight rules accommodate the division of heading into eight regions in polar coordinates, and the remaining three rules govern obstacle avoidance. The rules defining the fuzzy logic controller are as follows:
1. IF blink IS high THEN speed IS high
2. IF target Δx IS positive OR target Δx IS negative OR target Δy IS positive OR target Δy IS negative THEN speed IS high
3. IF target Δx IS zero AND target Δy IS zero THEN speed IS zero
4. IF target variability IS high OR blink IS low THEN speed IS low
5. IF target Δx IS positive AND target Δy IS zero THEN heading IS right
6. IF target Δx IS positive AND target Δy IS positive THEN heading IS up/right
7. IF target Δx IS positive AND target Δy IS negative THEN heading IS down/right
8. IF target Δx IS negative AND target Δy IS zero THEN heading IS left
9. IF target Δx IS negative AND target Δy IS positive THEN heading IS up/left
10. IF target Δx IS negative AND target Δy IS negative THEN heading IS down/left
11. IF target Δx IS zero AND target Δy IS positive THEN heading IS up
12. IF target Δx IS zero AND target Δy IS negative THEN heading IS down
13. IF obstacle distance IS zero THEN heading adjustment IS high
14. IF obstacle distance IS low THEN heading adjustment IS low
15. IF obstacle distance IS high THEN heading adjustment IS zero The first four rules govern the robot's speed. Higher blink rates imply a more focused operator intent and cause increased speed (rule 1). Conversely, high gaze variability or low blink rate imply a less sure target and lead to lower speed (rule 4). The greater the distance to the target, the higher the necessary speed to reach it in a timely manner, and speed should drop to zero as the target is reached (rules 2-3). It should be noted that lower speeds are sometimes desirable to conserve energy either when the goal is unclear or has been reached.

Rules 5-12 pertain to heading. These are relatively straightforward and use the four cardinal directions and the four semi-cardinal directions to navigate in the planar map based on the relative target distance in the x and y directions. This can be thought of as a fuzzy calculation of inverse tangent for the heading angle using target Δx and target Δy as inputs.

The remaining three rules (rules 13-15) constitute the robot's obstacle avoidance behavior. The closer the obstacle, the larger the heading adjustment applied to go around it. Whether this adjustment is added or subtracted from the heading variable is determined by whether the obstacle centroid is to the right or the left of the straight line along the robot's heading.

Figure 9:
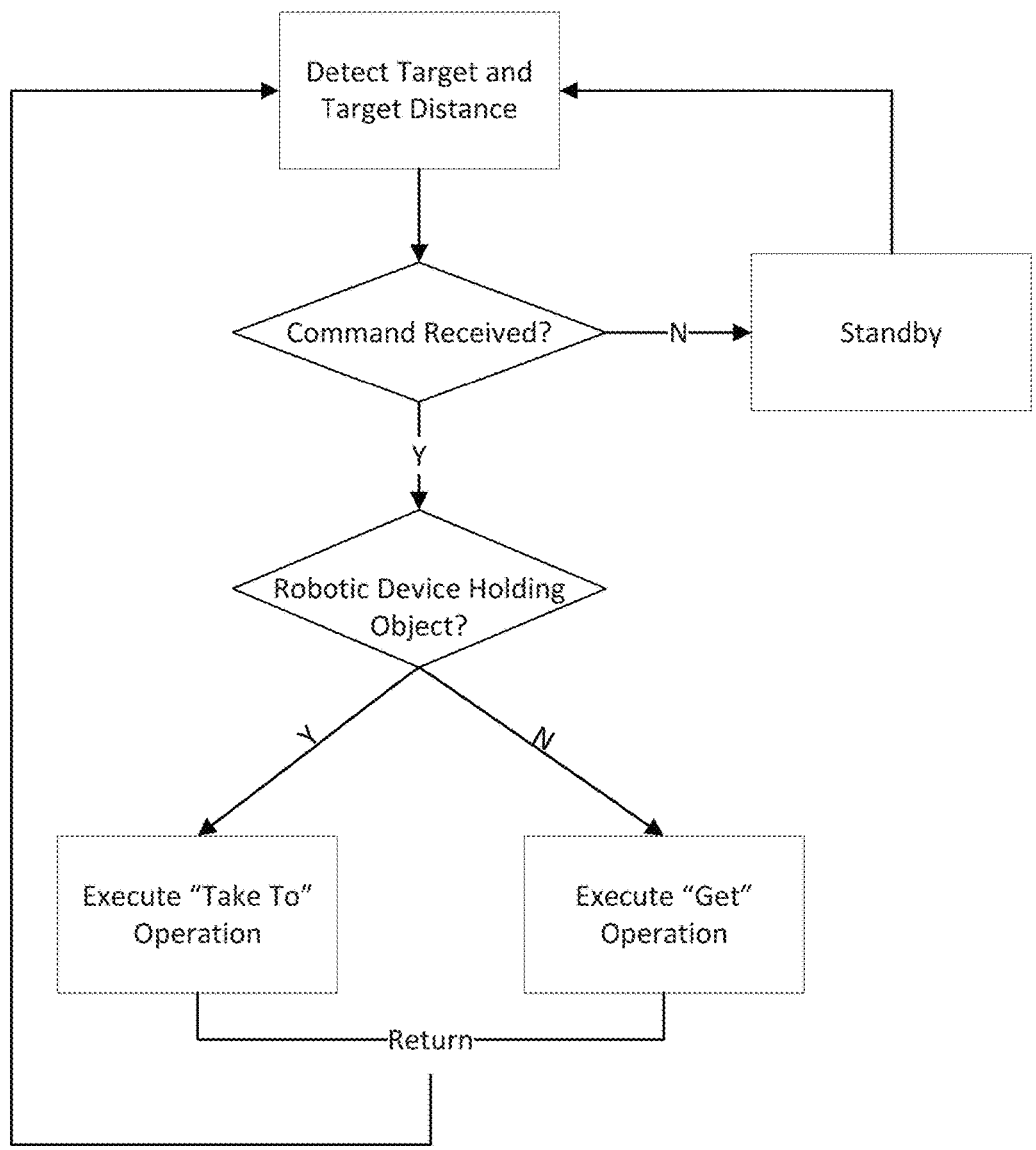
FIG. 9 one embodiment of a process for controlling a robot is depicted.

Referring now to FIG. 9, a process for controlling a robotic device such as a robotic hand, prosthetic, or the like, configured to assist with fetching and placing objects at the location of a gaze point. The gaze point, gaze distance, and gaze vector are determined in the substantially the same manner as discussed above with respect to FIGS. 1-8. The 3D gaze point locus may be used to control a robotic assistive device to place an object or pick up an object.

In step S1, the target distance and/or gaze point is detected in substantially the same way as discussed above with respect to FIG. 4. The process proceeds to step S2 to determine if a command has been received from the user. In some examples, the robotic device may perform a "take to" or "get" command based on the detected gaze point. For example, the "Take to" job is applied to the robot when the manipulation location is different from the current robot location and the robot is holding one object in hand; and the "Get" job is applied to the robot when the hand of the robot is free.

Accordingly, the robotic device may be configured with three safety rules. In one example, Rule 1 may be configured such that a standby job is enforced between two jobs. This rule forces the robot to confirm with the user before taking any action to avoid errors. Rule 2 may be configured so that the robot can only get, hold, or drop off one object at one time. This rule keeps the control procedures simple and reduces the control complexity for human beings. Rule 3 may be configured such that the "Take to" job is applied to the robot when the manipulation location is different from the current robot location and the robot is holding one object in hand; and the "Get" job is applied to the robot when the hand of the robot is free.

Returning to FIG. 9, if in step S2 a command is not received, the process proceeds to step S3 to remain in standby. If a command is received, the method proceeds to step S4 to determine if the robotic device is presently holding an object. If no object is being held, the method proceeds to Step S5 to execute a "take to" command. If in step S4 an object is being held, the method proceeds to step S6 to execute a "get" operation. Following steps S5 or S6, the method returns to step S1.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:
1. A method of creating control output signals from visual information comprising:
   monitoring one or more eyes of a user gazing at a target object;
   determining and measuring movement of the eye and pupil;
   analyzing the movement to identify intentional movement and unintentional movement;
   translating the movement into data describing three dimensional movement of the user's gaze;
   translating the data from the intentional movement into an output signal; and thereby
   creating an output signal.
2. The method of claim 1, wherein the analyzing involves the use of fuzzy logic.
3. The method of claim 1, wherein the output signal is transferred to a robot or assistive device.
4. The method of claim 3, wherein the robot or assistive device is controlled by one or more output signals.

5. The method of claim 1, wherein the monitoring is performed by an optical device.

6. The method of claim 1, the left and right eyes of the user are monitored to calculate a visual axis for each eye.

7. The method of claim 6, wherein an intersection of the two visual axes is determined.

8. The method of claim 7, wherein the intersection is used to calculate a gaze vector.

9. The method of claim 8, wherein the gaze vector is used to calculate a gaze distance along the gaze vector.

10. The method of claim 6, wherein the shortest distance between non-intersecting visual axes is determined.

11. The method of claim 10, wherein the intersection is used to calculate a gaze vector.

12. The method of claim 11, wherein the gaze vector is used to calculate a gaze distance along the gaze vector.

\* \* \* \* \*